US006168869B1

(12) United States Patent
Tomioka et al.

(10) Patent No.: US 6,168,869 B1
(45) Date of Patent: Jan. 2, 2001

(54) ANTI-MICROBIAL ALUMINUM PRODUCT AND METHOD FOR PRODUCING THE SAME

(75) Inventors: Toshikazu Tomioka, Ibaraki; Akihiko Yoshida, Hirakata, both of (JP)

(73) Assignee: Matsushita Electric Industrial Co., Ltd., Osaka (JP)

(*) Notice: Under 35 U.S.C. 154(b), the term of this patent shall be extended for 0 days.

(21) Appl. No.: 09/073,432

(22) Filed: May 6, 1998

(51) Int. Cl.$^7$ .............................. B32B 9/00; A01N 59/00; C25D 11/04; B05D 1/18
(52) U.S. Cl. ....................... 428/469; 428/472.2; 428/907; 428/472; 424/414; 424/618; 424/630; 424/641; 424/711; 427/419.2; 427/435; 205/324
(58) Field of Search ................ 428/305.5, 469, 428/472.2, 907; 424/404, 414, 421, 618, 630, 637, 641, 711; 427/419.2, 435; 205/324

(56) References Cited

U.S. PATENT DOCUMENTS

| 5,429,819 | * | 7/1995 | Oka et al. ........................... 424/400 |
| 5,510,109 | * | 4/1996 | Tomioka et al. .................... 424/421 |
| 5,645,846 | * | 7/1997 | Oka et al. ........................... 424/405 |
| 5,651,978 | * | 7/1997 | Tomioka et al. .................... 424/421 |

FOREIGN PATENT DOCUMENTS

| 62-182298 | 8/1987 | (JP) . |
| 04084852 | 3/1992 | (JP) . |
| 07305178 | 11/1995 | (JP) . |
| 09125284 | 5/1997 | (JP) . |

* cited by examiner

Primary Examiner—Timothy M. Speer
Assistant Examiner—Bryant Young
(74) Attorney, Agent, or Firm—McDermott, Will & Emery

(57) ABSTRACT

The present invention relates to an improvement in an anodic aluminum oxide coating on which microbials are easy to adhere and propagate, for constantly keeping it clean. The present invention provides an anti-microbial aluminum product comprising: a porous oxide coating covering the surface of the aluminum core for the product and an inorganic bacteria controlling ingredient being carried in the micropores of the oxide coating. The anodic oxide coating is preferably sealed.

15 Claims, No Drawings

ANTI-MICROBIAL ALUMINUM PRODUCT AND METHOD FOR PRODUCING THE SAME

BACKGROUND OF THE INVENTION

The present invention relates to an aluminum product having an improved anodic oxide coating and a method for producing the same.

In the past, aluminum had widely been used as table wares. Nowadays, it has also been applied to architectural materials ranging from interior components including door knobs to window sashes, and are indispensable as the architectural materials and items. In addition, aluminum is also applied to heat-transfer fins of air conditioners and the like due to an advantage of high heat-conductivity.

In general, in order to prevent an aluminum product from corrosion, there is formed an anodic aluminum oxide coating (known as the registered trade name "ALUMITE") made of aluminum oxide on surfaces of the aluminum product. The anodic oxide coating has a high hydrophilic property and thus a microbial accompanying water is easy to adhere to the coating.

The architectural components are frequently touched by hands of unspecified number of persons. Furthermore, they have little occasion to be washed because they are hard to be detached. Therefore, when aluminum is applied to the architectural material, the microbials adhered to the surface of the material are liable to propagate thereon.

BRIEF SUMMARY OF THE INVENTION

The object of the present invention is to solve the above-mentioned problems and provides an aluminum product which has a constantly clean anodic oxide coating.

The present invention provides an anti-microbial aluminum product that has a porous anodic oxide coating carrying an inorganic bacteria controlling ingredient in the micropores.

The present invention also provides a method for producing an anti-microbial aluminum product comprising the steps of:
  forming an oxide coating on a surface of an aluminum core for the product by anodically polarizing the aluminum core in an electrolyte solution; and
  making an inorganic bacteria controlling ingredient be carried in micropores of the oxide coating by immersing the aluminum core in a solution containing an inorganic bacteria controlling ingredient.

In a preferred mode of the method for producing an anti-microbial aluminum product, the method further comprises the step of sealing the surface of the oxide coating.

The present invention makes the inorganic bacteria controlling ingredient be carried in the micropores with a diameter of 10 to 20 nm existing in the anodic oxide coating of the aluminum product. For an aluminum product to be applied to use accompanying a contact with water, the aluminum core is further subjected to the sealing treatment of the anodic oxide coating so as to prevent the bacteria controlling ingredient from falling off. By this treatment, the anti-microbial property of the aluminum product can be maintained for a long period.

This sealing of the anodic oxide coating does not mean a complete occlusion of the micropores containing the bacteria controlling ingredient. The bacteria controlling ingredient is gradually released from the micropores through minute gaps remaining after the sealing, and the released bacteria controlling ingredient demonstrates a performance of preventing the propagation of the microbials. For a product with no occasion of coming in contact with water, the above-mentioned sealing treatment is not necessarily required.

In another preferred mode of the present invention, a compound of at least one metal selected from the group consisting of silver, copper and zinc is used as the bacteria controlling ingredient which gives the anti-microbial property to the anodic oxide coating of the aluminum product. Among the compounds, a thiosulfato complex, in particular silver thiosulfato complex, is preferable. A solution of silver thiosulfato complex is preferably prepared by adding potassium sulfite to a saturated aqueous solution of silver acetate, then adding potassium thiosulfate to the aqueous solution. Here, silver acetate, potassium sulfite and potassium thiosulfate may be mixed in a molar ratio of 1:3:3.

The silver thiosulfato complex is absorbed to the surface of the anodic oxide coating and firmly adhered thereon since the anodic oxide coating is charged positively and the silver thiosulfato complex is an anion. In addition, since the silver thiosulfato complex is an anion, it has a low reactivity with chlorine and hardly reacts with a chlorine bleaching agent, sweat on the hands, other chemicals such as an invert soap (benzalkonium chloride) which is frequently used in medical institution, or the like. Therefore, the anti-microbial property is maintained for a long period when the silver thiosulfato complex is employed as the bacteria controlling ingredient.

Furthermore, the silver thiosulfato complex has advantages of colorlessness and of a higher stability against light as compared with the other silver salts, and another advantage of being stabilized still more in color change on aging when it is once adsorbed on the anodic oxide coating.

The silver thiosulfatocomplex has another advantage of high safety. It has a low acute toxicity with $LD_{50}$ of larger than 2,000 mg/kg, and shows negativity to both primary skin irritation test and mutagenicity test. Further, it requires less care in environmental pollution. Thus, a great value is brought to the industry, in a case of applying the silver thiosulfato complex to the bacteria controlling ingredient.

Therefore, the silver tiosulfatocomplex is particularly suited for the bacteria controlling ingredient.

In another preferred mode of the present invention, the anti-microbial aluminum product further comprises an organic anti-fungal agent of low molecular weight carried in said micropores.

In still another preferred mode of the present invention, an organic anti-fungal agent of low molecular weight such as 2-(4-thiazolyl)-benzimidazole (hereinafter referred to as "TBZ") is also used in addition to the bacteria controlling ingredient. It is preferable to immerse the anodic oxide coating into a polar solvent solution of TBZ or an aqueous dispersion thereof to give the oxide coating an anti-fungal property.

Further, a dye may be contained in the solution of the bacteria controlling ingredient.

In one of the methods for sealing the anodic oxide coating carrying the bacteria controlling ingredient, the anodic oxide coating is immersed in the above-mentioned aqueous solution of silver thiosulfato complex at a temperature of not less than 80° C. for about 10 minutes. The sealing treatment may also be carried out by immersing the anodic oxide coating in a hot water. However, in order to prevent the complex once adsorbed in the micropores from diffusing into the water, it is preferable to carry the sealing treatment by using an aqueous solution of silver thiosulfato complex at a higher temperature of not less than 80° C. which is higher than that of the aqueous solution of silver thiosulfato complex used in the previous step of making the complex be carried.

In another method for sealing the anodic oxide coating, the anodic oxide coating is immersed in a solution containing at least one member selected from the group consisting of an acetate of nickel, acetate of cobalt and chromates thereof at not less than 80° C. for not less than 3 minutes.

In still another method for sealing the anodic oxide coating, the anodic oxide coating is immersed in a reactive organic silicone compound such as tetraethoxysilane or the like, and the reactive organic silicone compound is hydrolyzed on the surface of the anodic oxide coating thereby to produce silicon dioxide. As the reactive organic silicone compound used here, an alcohol solution of tetraethoxysilane is suitable.

Usually, the anodic oxide coating is industrially produced by a series of treatments of degreasing, anodizing, sealing, washing with water and painting, after the substrate plate of aluminum has been worked to have a desired shape. Any of a sulfuric acid method, oxalic acid method, chromic acid method, organic acid-added sulfuric acid method or the like known as a method for forming the anodic oxide coating can be applied to the present invention. The thickness of the anodic oxide coating to be formed is preferably 7 to 20 $\mu$m.

While the novel features of the invention are set forth particularly in the appended claims, the invention, both as to organization and content, will be better understood and appreciated, along with other objects and features thereof, from the following detailed description.

DETAILED DESCRIPTION OF THE INVENTION

In the following paragraphs, a description will be made on the preferred embodiments of the present invention in a case of using an anodic aluminum oxide coating formed by a sulfuric acid method.

EXAMPLE 1

First, a description will be made on a method of preparing a bacteria controlling solution.

By dissolving silver acetate in pure water at 40° C., a saturated aqueous solution of silver acetate was prepared. Next, by dissolving potassium sulfite and potassium thiosulfate in this aqueous solution, an aqueous solution of silver thiosulfato complex was prepared.

On the other hand, as the above-mentioned manner, anodic aluminum oxide coatings with a thickness of about 10 $\mu$m were formed on both surfaces of an aluminum substrate. Then, the aluminum substrate was immersed in the aqueous solution of silver thiosulfato complex maintained at 40° C. for 10 minutes. By this procedure, the silver thiosulfato complex was adsorbed in the micropores in the anodic oxide coating. Next, the aluminum substrate was taken up from the solution and roughly washed with water.

A solution was prepared by mixing tetraethoxysilane (hereinafter referred to as "TEOS") with ethanol in a ratio of 1:1 by weight, and the aluminum substrate was immersed in this solution for 5 minutes. The TEOS in the solution was hydrolyzed with water remaining in the anodic oxide coating or the micropores, then silicon dioxide was precipitated on the anodic oxide coating. With this precipitated silicon dioxide, the micropores on the surfaces of the oxide coating were sealed. In a case that the surface of the product to be obtained is coated with a resin paint, it is needless to say that the aluminum substrate exhibits more excellent property when the anti-microbial component is also added to the resin paint.

Here, a description will be made on the proportion of the raw materials for preparing the silver thiosulfato complex as the bacteria controlling ingredient. By adding potassium sulfite to a silver acetate aqueous solution, silver thiosulfato complex is synthesized. Further, by adding potassium thiosulfate to this solution, the silver thiosulfato complex is converted into the silver thiosulfato complex. Here, it is desirable to mix the silver acetate with the potassium sulfite in a molar ratio of 1:3. If the amount of the potassium sulfite is smaller than this ratio, the complex is not formed and the solution turns brown.

Various kinds of solutions where the molar ratio of the silver acetate and the potassium sulfite is kept constant to 1:3 while the molar ratio of the potassium thiosulfate being varied were prepared. Then, the aluminum substrates were treated with the solutions.

Surface conditions and anti-microbial performances of the aluminum substrates with the anodic oxide coating were examined. The results are listed in

TABLE 1

| | Anti-microbial Performance | | |
|---|---|---|---|
| Molar Ratio | Escherichia coli | Staphylococcus aureus | Surface Condition |
| 1:3:1 | X | X | X |
| 1:3:2 | Δ | ○ | ⊚ |
| 1:3:3 | ⊚ | ⊚ | ⊚ |
| 1:3:4 | X | X | X |
| 1:3:5 | Δ | ○ | ⊚ |
| 1:3:6 | ○ | ⊚ | ⊚ |
| 1:3:8 | ○ | ○ | ⊚ |

Molar ratio = silver acetate:potassium sulfite:potassium thiosulfate
Anti-microbial performance
⊚: number of colony formation units (CFU)/ml = 0
○: number of CFU/ml = 1–50
Δ: number of CFU/ml = 51–500
X: number of CFU/ml > 501

As shown in Table 1, the optimum mixing ratio of silver acetate, potassium sulfite and potassium thiosulfate is 1:3:3 in molar ratio.

Next, an anodic oxide coating with varied thickness was formed on the aluminum substrate. Thus treated aluminum substrates were immersed in the solution containing silver acetate, potassium sulfite and potassium thiosulfate in molar ratio of 1:3:3 and the aluminum substrates were also examined in the same manner. The results are listed in Table 2.

TABLE 2

| | Anti-microbial Performance | | |
|---|---|---|---|
| Thickness ($\mu$m) | Escherichia coli | Staphylococcus aureus | Surface Condition |
| 5 | ⊚ | ⊚ | X |
| 7 | ⊚ | ⊚ | ○ |
| 10 | ⊚ | ⊚ | ⊚ |
| 20 | ⊚ | ⊚ | ⊚ |
| 30 | ⊚ | ⊚ | ○ Colored |

Anti-microbial performance
⊚: Number of CFU/ml = 0
○: Number of CFU/ml = 1–50
Δ: Number of CFU/ml = 51–500
X: Number of CFU/ml > 501

As shown in Table 2, the thickness of the anodic oxide coating is preferably 7 to 20 $\mu$m, and 10 $\mu$m is the optimum.

EXAMPLE 2

After immersing an aluminum substrate provided with an anodic oxide coating having a thickness of 5 to 30 $\mu$m thereon in an aqueous solution of silver thiosulfato complex in a manner similar to Example 1, the aluminum substrate was immersed in another aqueous solution of silver thiosulfato complex at 80° C. for 10 minutes. The aqueous solution of silver thiosulfato complex used here has been prepared by mixing silver acetate, potassium sulfite and potassium thiosulfate at molar ratio of 1:3:3.

The aluminum substrates immersed in the solutions were examined as same in Example 1. As a result, the aluminum substrate with the anodic oxide coating having a thickness of 10 μm also demonstrated an excellent performance.

Incidentally, by adding a dye to the solution of silver tiosulfatocomplex, the anti-microbial anodic oxide coating can be colored.

EXAMPLE 3

Aluminum substrates provided with an anodic oxide coating having a thickness of 5 to 30 μm thereon were immersed in an aqueous solution of silver tiosulfatocomplex in a manner similar to Example 2, then the aluminum substrates were further immersed in a solution of nickel acetate heated to 80° C. for 5 minutes. Thus treated aluminum substrates were examined as in Example 1.

In this case, the aluminum substrate with the anodic oxide coating having a thickness of 10 μm demonstrated an excellent performance.

A similar technical advantage can be obtained by using, in place of nickel acetate, a cobalt acetate, nickel chromate, cobalt chromate or their combination.

EXAMPLE 4

Procedure used in Example 1 was followed except for further addition of an aqueous dispersion of 2-(4-thiazolyl)-benzimidazole (hereinafter referred to as "TBZ") to the aqueous solution of silver tiosulfatocomplex. When the aluminum substrate is immersed in the mixture solution, the TBZ contained in the mixture solution penetrates into the micropores of the anodic oxide coating. Therefore, the TBZ was also be carried in the anodic oxide coating of the aluminum substrate by this treatment. Since TBZ exhibits an anti-fungal property, the anti-fungal property was given to an anodic oxide coating in addition to the anti-microbial property.

It is needless to say that a similar technical advantage can be obtained by using, in place of TBZ, other organic anti-fungal agent of low molecular weight.

As described above, according to the present invention, it is possible to give the aluminum product anti-microbial property on its surface in addition to such a physical feature as an anti-corrosion property. Therefore, when the anti-microbial aluminum product in accordance with the present invention is applied to life-related materials, architectural materials, heat-transfer fin unit of air conditioner or the like, it is possible to contribute to an improvement in the cleanness of the living space.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. An anti-microbial aluminum product comprising:
   a porous oxide coating, formed by anodic polarizing, covering the surface of an aluminum core; and
   an inorganic bacteria controlling ingredient carried in micropores of said porous oxide coating.

2. An anti-microbial aluminum product comprising:
   a porous oxide coating, formed by anodic polarizing, covering the surface of an aluminum core; and
   an inorganic bacteria controlling ingredient adsorbed in micropores of said porous oxide coating, said micropores being sealed.

3. The anti-microbial aluminum product in accordance with claim 1, wherein said bacteria controlling ingredient comprises a compound of at least one metal selected from the group consisting of silver, copper and zinc.

4. The anti-microbial aluminum product in accordance with claim 1, wherein said bacteria controlling ingredient is silver thiosulfato complex.

5. The anti-microbial aluminum product in accordance with claim 1, further comprising an organic anti-fungal agent of low molecular weight carried in said micropores.

6. The anti-microbial aluminum product in accordance with claim 1, wherein said coating has a thickness of 7 to 20 μm.

7. A method for producing an anti-microbial aluminum product comprising the steps of:
   forming an oxide coating on a surface of an aluminum core by anodically polarizing said aluminum core in an electrolyte solution; and
   introducing an inorganic bacteria controlling ingredient into micropores of said oxide coating by immersing said aluminum core in a solution containing said inorganic bacteria controlling ingredient.

8. The method for producing an anti-microbial aluminum product in accordance with claim 7, further comprising the step of sealing said micropores in which said bacteria controlling ingredient is introduced.

9. The method for producing an anti-microbial aluminum product in accordance with claim 8, wherein said solution containing an inorganic bacteria controlling ingredient is an aqueous solution of silver thiosulfato complex, and said micropores are sealed by immersing said aluminum core in an aqueous solution of silver thiosulfato complex at a temperature of not less than 80° C. which is higher than that of the aforementioned aqueous solution of silver thiosulfato complex.

10. The method for producing an anti-microbial aluminum product in accordance with claim 8, wherein said micropores are sealed by immersing said aluminum core in a solution containing at least one member selected from the group consisting of nickel acetate, cobalt acetate, nickel chromate and cobalt chromate at not less than 80° C. for not less than 3 minutes.

11. The method for producing an anti-microbial aluminum product in accordance with claim 8, wherein said micropores are sealed by immersing said aluminum core in a reactive organic silicone compound and hydrolyzing said reactive organic silicone compound on the surface of said oxide coating to produce silicon dioxide.

12. The method for producing an anti-microbial aluminum product in accordance with claim 7, wherein said oxide coating has a thickness of 7 to 20 μm.

13. The anti-microbial aluminum product in accordance with claim 1, wherein said inorganic bacteria controlling ingredient is thiosulfato complex of at least one metal selected from the group consisting of silver, copper, and zinc.

14. The anti-microbial aluminum product in accordance with claim 5, wherein said organic anti-fungal agent is 2-(4-thiazolyl)-benzimidazole.

15. The anti-microbial aluminum product in accordance with claim 1, wherein said micropores are sealed by the method of immersing an aluminum core, having a coating whose deep holes are filled with thiosulfato complex, in an aqueous solution of silver thiosulfato complex at a temperature of not less than 80° C.

* * * * *